(12) United States Patent
Poplin et al.

(10) Patent No.: US 8,777,962 B1
(45) Date of Patent: Jul. 15, 2014

(54) CIRCUMCISION APPARATUSES AND METHODS

(75) Inventors: J. Dale Poplin, Draper, UT (US);
Woodrow L. Blevins, Draper, UT (US);
Thomas Crabtree, Kailua, HI (US);
Mark Filstein, New York, NY (US)

(73) Assignee: MedSurg Technology LLC, Draper, UT (US)

( * ) Notice: Subject to any disclaimer, the term of this patent is extended or adjusted under 35 U.S.C. 154(b) by 259 days.

(21) Appl. No.: 12/756,817

(22) Filed: Apr. 8, 2010

Related U.S. Application Data

(60) Provisional application No. 61/167,599, filed on Apr. 8, 2009.

(51) Int. Cl.
*A61B 17/326* (2006.01)

(52) U.S. Cl.
USPC .......................................................... 606/118

(58) Field of Classification Search
USPC .......................................................... 606/118
See application file for complete search history.

(56) References Cited

U.S. PATENT DOCUMENTS

| | | | |
|---|---|---|---|
| 1,765,319 A | 6/1930 | Williams | |
| 3,072,126 A * | 1/1963 | Fenton | 606/118 |
| 3,111,124 A | 11/1963 | Rodbard | |
| 3,612,057 A | 10/1971 | Freedman | |
| 3,625,218 A * | 12/1971 | Valinoti, Jr. | 606/45 |
| 4,491,136 A | 1/1985 | LeVeen | |
| 5,163,943 A | 11/1992 | Mohiuddin et al. | |
| 5,439,466 A | 8/1995 | Kilejian | |
| 5,676,672 A | 10/1997 | Watson et al. | |
| 5,797,921 A | 8/1998 | Cimini et al. | |
| 5,860,988 A | 1/1999 | Rawlings | |
| 6,660,012 B2 | 12/2003 | Lahiji | |
| 6,740,095 B2 | 5/2004 | Watson, Jr. et al. | |
| 2004/0215210 A1 * | 10/2004 | Duel | 606/118 |
| 2008/0021482 A1 * | 1/2008 | Tomlinson | 606/118 |

* cited by examiner

*Primary Examiner* — Kathleen Holwerda
*Assistant Examiner* — Sarah W Aleman
(74) *Attorney, Agent, or Firm* — Thorpe North & Western LLP

(57) ABSTRACT

A circumcision device comprises a base, configured to engage a patient's body adjacent the patient's penis, and at least one support arm, extending from the base. A cutting assembly is carried by or on the at least one support arm, the cutting assembly being moveable relative to the base along the support arm. A cutting element is carried by the cutting assembly, the cutting element being operable to cut tissue of the penis to facilitate removal of the foreskin from the penis.

10 Claims, 4 Drawing Sheets

CIRCUMCISION APPARATUSES AND METHODS

PRIORITY CLAIM

Priority is claimed of U.S. Provisional Patent Application Ser. No. 61/167,599, filed Apr. 8, 2009, which is hereby incorporated herein by reference in its entirety.

FIELD OF THE INVENTION

1. Background

The present invention relates generally to systems for performing male circumcisions. More specifically, the present invention relates to such systems that are suitable for use with adult male patients.

2. Related Art

Male circumcision is a procedure in which the foreskin, which protects the head (or glans) of the penis, is physically removed. While many circumcisions are performed for religious purposes, circumcisions are recognized by many as medically beneficial procedures.

For example, it has been shown that circumcision prevents infection and inflammation of the foreskin, and appears to decrease the risk of cancer of the penis. Some studies have shown a greater risk of cervical cancer in female sexual partners of uncircumcised men who are infected with human papillomavirus, a condition for which the risk can be lowered by male circumcision. Circumcision may also have a role in reducing the risk of contracting sexually transmitted diseases.

While various circumcision procedures have been practiced for many years, these techniques often involve manual cutting of the foreskin using a scalpel. Such manual techniques can lead to inconsistent results from one patient to another, a higher degree of risk to the patient, and often require the services of a high-cost surgeon.

SUMMARY OF THE INVENTION

The present invention provides a circumcision device, including a base, configured to engage a patient's body adjacent the patient's penis and at least one support arm, extending from the base. A cutting assembly can be carried by or on the at least one support arm, the cutting assembly being moveable relative to the base along the support arm. A cutting element can be carried by the cutting assembly, the cutting element operable to cut tissue of the penis to facilitate removal of the foreskin from the penis.

In accordance with another aspect of the invention, a method of circumcising a penis is provided, including engaging a patient's body adjacent the patient's penis with a support base; engaging the penis with a clamping assembly; moving the clamping assembly away from the base along at least one support arm extending from the base to thereby stretch the penis into an at least partially taut condition; and engaging tissue of the penis with a cutting element carried by the at least one support arm to cut at least a portion of the tissue.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Figure 1:
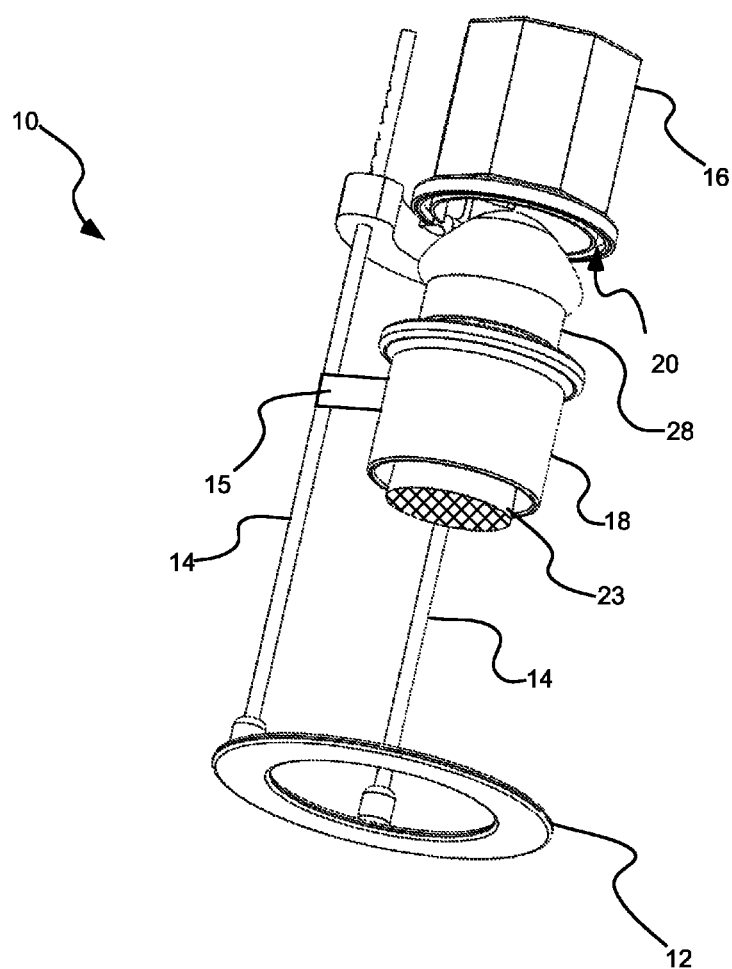
FIG. 1 is a perspective view of a circumcision device in accordance with an embodiment of the invention.

Before the present invention is disclosed and described, it is to be understood that this invention is not limited to the particular structures, process steps, or materials disclosed herein, but is extended to equivalents thereof as would be recognized by those of ordinarily skilled in the relevant arts. It should also be understood that terminology employed herein is used for the purpose of describing particular embodiments only and is not intended to be limiting.

It must be noted that, as used in this specification and the appended claims, the singular forms "a" and "the" include plural referents, unless the context clearly dictates otherwise. Thus, for example, reference to a "cutting element" can include reference to one or more of such cutting elements.

DEFINITIONS

In describing and claiming the present invention, the following terminology will be used in accordance with the definitions set forth below.

Relative directional terms, such as "upper," "lower," "top," bottom," etc., are used herein to aid in describing various features of the present circumcision systems. It is to be understood that such terms are generally used in a manner consistent with the understanding one of ordinary skill in the art would have of the use and typical orientation of such systems. Such terms should not, however, be construed to limit the present invention.

As used herein, the term "substantially" refers to the complete, or nearly complete, extent or degree of an action, characteristic, property, state, structure, item, or result. As an arbitrary example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. As another arbitrary example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "slightly above" or "slightly below" the endpoint.

Distances, forces, weights, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 inch to about 5 inches" should be interpreted to include not only the explicitly recited values of about 1 inch to about 5 inches, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value and should apply regardless of the breadth of the range or the characteristics being described.

Invention

The present invention provides systems for performing male circumcisions. The systems can be utilized in a variety of settings and with a variety of patients, but have been found to be particularly effective for performing circumcisions on adult males. The systems provide a safe, efficient and accurate method of performing circumcisions, and can be used in settings with less-than-desirable hygienic conditions (e.g., "in the field"). The systems can be operated by personnel with relatively minimum levels of training (e.g., a trained surgeon is not necessarily required).

Figure 2:
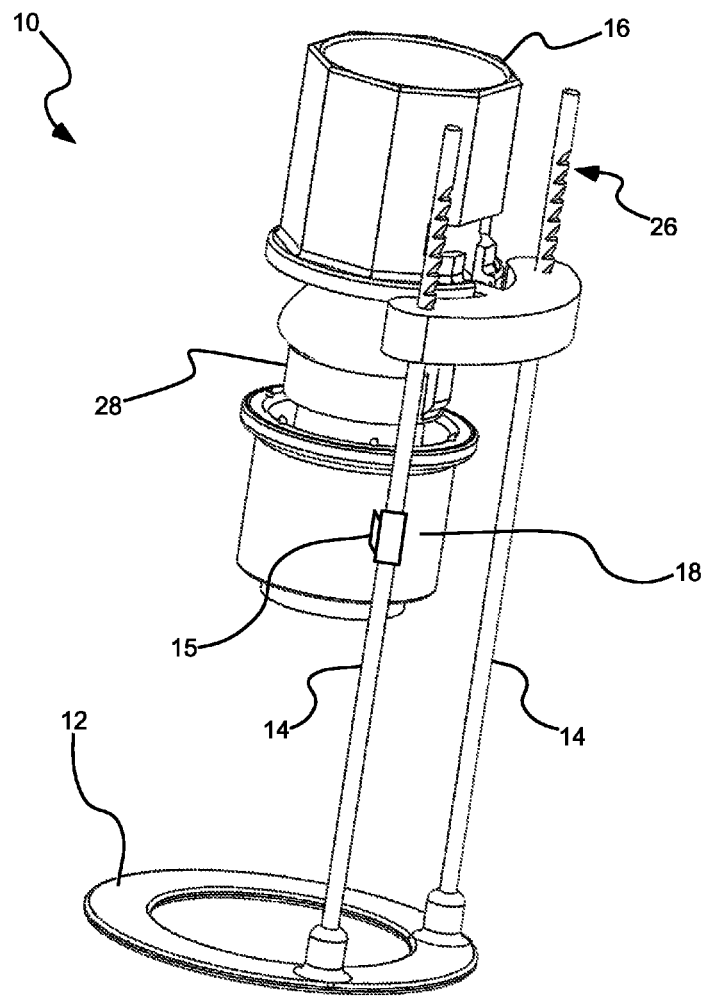
FIG. 2 is a perspective view of the circumcision device of FIG. 1, shown rotated from the position of FIG. 1.

As shown generally in FIGS. 1 and 2, in one embodiment of the invention, a circumcision device 10 is provided that can include a base 12. The base 12 is operable to engage a patient's body (not shown) adjacent an area from which the patient's penis (a portion of which is shown at 23 in FIG. 1) extends from the torso (not shown). The device can include at least one support arm 14 (note that two support arms are included in the example shown in the figures) that can extend from the base. A cutting assembly 16 can be carried by or on the at least one support arm (or on or by both support arms). The cutting assembly can be moveable relative to the base along the support arm. A cutting element 20 can be carried by the cutting assembly, the cutting element being generally operable to cut or incise tissue of the penis to facilitate removal of the foreskin from the penis.

Figure 3:
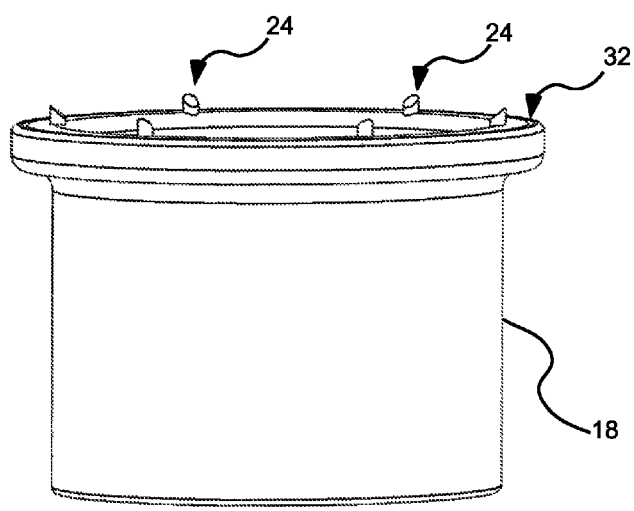
FIG. 3 is a more detailed, side view of a portion of a clamping assembly in accordance with an aspect of the invention.

The system can also include a clamping assembly 18 which can also be carried by the at least one support arm 14 via one or more arms 15. The clamping assembly can be operable to clamp a portion of the penis, or tissue of the penis, to restrain the tissue to allow a precise cut or incision to be made during the circumcision process. The clamping assembly can be configured so as to maintain engagement with the penis tissue after cutting of the tissue to facilitate stitching of the tissue. Thus, the clamping assembly can be operable to both engage the penis during the cutting process, and maintain engagement after the cutting has been completed to enable suturing or stitching of the cut portions of tissue. To facilitate this process, one or engagement teeth (24 in FIG. 3) can be provided on the clamping assembly to provide "one way" engagement with the penis tissue (e.g., the foreskin or tissue of the penis can easily be stretched over the engagement teeth, but will not as easily slide off the engagement teeth due to the angled position of the engagement teeth).

A series of stops (26 in FIG. 2) can be provided on the support arms and can be operable to selectively fix a position of the cutting assembly relative to the base. As discussed in more detail below, the penis is generally stretched taut prior to performing the circumcision—the stops can be engaged after the head of the penis is moved away from the base 12 of the device to secure the head of the penis distally from the torso of the patient. Thus, the cutting assembly 16 can be reliable held in position relative to the base during the cutting operation. While the stops 26 are used in one embodiment, in other embodiments, the cutting assembly and/or an engagement band 28 can include engagement or locking structure that locks onto the support arm to temporarily fix the cutting assembly relative to the base. Suitable locking structure can include, without limitation, biased clamps pin-and-slot arrangements, etc.

Figure 4:
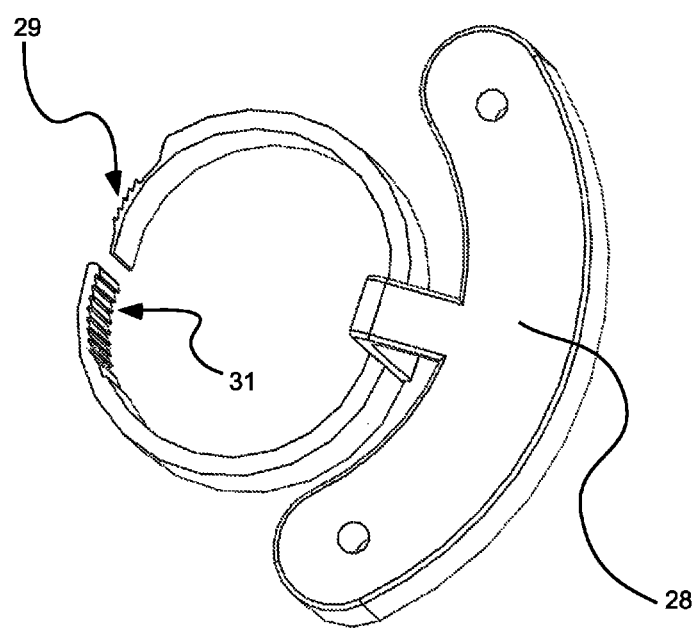
FIG. 4 is a top view of an exemplary engagement band in accordance with an embodiment of the invention.

An engagement band 28 can be carried by the cutting assembly and can be operable to engage a portion of the body 23 of the penis to facilitate stretching of the penis into an at least partially taut condition. Generally, the engagement ring or band will engage the penis body below the glans 30. The engagement band can be openable (e.g., spreadable) to allow the penis to be inserted into the band, after which the band can be tightened to securely grasp the penis body. One exemplary engagement band is shown in FIG. 4. Interlocking structure 29, 31 can be included on the engagement band to allow temporary but secure attachment of the band about the body of the penis.

In a typical use of the system, the base 12 of the device will be placed against the torso of the patient, encircling the penis. The clamping assembly 18 can then be placed over the penis and slid onto or adjacent the base. The cutting assembly 16 can then be slid over the top of the penis (while engaged with the support arms) to allow the engagement band 28 to be wrapped bout and secured to the body of the penis. The penis can then be pulled into an at least partially taut condition by moving the cutting assembly (specifically, the engagement band) away from the base of the device (resulting in the engagement band stretching the body of the penis).

After this, the clamping assembly 18 can be moved adjacent to and around the engagement ring 28. The foreskin of the penis can then be folded downwardly and around the clamping assembly into a taut condition. When a blade is used as the cutting element 20, the cutting blade can then be engaged with the penis tissue on top of the clamping assembly and rotated relative to the clamping assembly to cut this tissue. After cutting, the engagement teeth 24 of the clamping assembly will maintain engagement of the foreskin tissue, allowing suturing of the tissue in the location where the cut was made.

A mating groove 32 can be formed in the clamping assembly 18. The cutting blade 20 can engage this mating groove (through or on top of the penis tissue immediately adjacent the groove) to enable the cutting blade to more easily and cleanly cut the penis tissue.

In the example shown, the cutting element 20 comprises a cutting blade that can be formed in a generally annular shape. The cutting blade can extend substantially completely around the cutting assembly as an integral unit. Alternately, the cutting blade can include a series of blades arranged about the periphery of the cutting assembly (e.g., one or more gaps may be disposed between adjacent blade cutting elements). Other suitable cutting elements can also be used, including, without limitation, electrosurgical cutting/sealing elements and the like.

In addition to the structural elements described above, the present invention also provides a method of circumcising a penis, comprising engaging a patient's body adjacent the patient's penis with a support base, and engaging the penis with a clamping assembly. The method can include moving the clamping assembly away from the base along at least one support arm extending from the base to thereby stretch the penis into an at least partially taut condition. The tissue of the penis can be engaged with or by a cutting element carried by the at least one support arm to cut at least a portion of the tissue.

The method can further include suturing or otherwise treating tissue of the penis while at least a portion of the tissue remains clamped by the clamping assembly. Engaging the stretched tissue of the penis with the cutting element can include inserting a cutting blade within a channel formed in an opposing portion of the cutting assembly. The cutting blade can comprise an annular cutting blade, or an electrosurgical cutting and/or sealing element. Electrosurgical cutting elements can advantageously be used to simultaneously (or nearly simultaneously) cut and seal the tissue, reducing or eliminating the need to suture or stitch the treated area.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

We claim:

1. A circumcision device, comprising:
   a base, configured to engage a patient's torso adjacent the patient's penis;
   at least one support arm, extending from the base;
   a cutting assembly, carried by or on the at least one support arm, the cutting assembly being moveable relative to the base along the support arm;
   a cutting element, carried by the cutting assembly, the cutting element operable to cut tissue of the penis to facilitate removal of the foreskin from the penis; and
   a clamping assembly, carried by the at least one support arm, the clamping assembly operable to clamp at least a portion of tissue of the penis while the clamping assembly is moved along the support arm to thereby stretch the body of the penis into a substantially taut condition between the base engaging the patient's torso and the clamping assembly.

2. The device of claim 1, wherein the clamping assembly is operable to maintain engagement with at least a portion of the penis tissue after cutting of the tissue to facilitate suturing or treatment of the tissue after cutting of the tissue.

3. The device of claim 1, wherein the clamping assembly includes at least one engagement tooth, operable to engage and at least partially restrain penis tissue.

4. The device of claim 1, wherein the at least one support arm includes a series of stops operable to selectively fix a position of the cutting assembly relative to the base.

5. The device of claim 1, wherein the cutting assembly includes engagement structure, operable to engage the support to selectively fix a position of the cutting assembly relative to the base.

6. The device of claim 1, wherein the clamping assembly includes an engagement band, operable to fit around the penis and engage the penis below the glans.

7. The device of claim 1, wherein the cutting element comprises an annular blade.

8. The device of claim 7, wherein the cutting assembly includes a mating groove, sized and shaped to receive therein the annular blade.

9. The device of claim 1, wherein the cutting element comprises an electrosurgical cutting element.

10. A circumcision device, comprising:
    a base, configured to engage a patient's torso immediately adjacent the patient's penis;
    at least one support arm, extending in a substantially vertical direction from the base, substantially orthogonally to the patient's torso;
    a cutting assembly, carried by or on the at least one support arm, the cutting assembly being vertically moveable relative to the base along the support arm;
    a cutting element, carried by the cutting assembly, the cutting element operable to cut tissue of the penis to facilitate removal of the foreskin from the penis; and
    a clamping assembly, carried by the at least one support arm, the clamping assembly operable to clamp at least a portion of tissue of the penis while the clamping assembly is moved vertically along the support arm and vertically away from the base, to thereby stretch the body of the penis into a substantially taut, vertical condition between the base engaging the at least a portion of the patient's torso and the clamping assembly.

* * * * *